(12) United States Patent
Chan et al.

(10) Patent No.: US 7,943,170 B2
(45) Date of Patent: May 17, 2011

(54) SUSTAINED RELEASE PARACETAMOL CONTAINING COMPOSITIONS

(75) Inventors: Shing Yue Chan, Parsippany, NJ (US); Timothy James Grattan, Weybridge (AU); Bounkhiene Sengmanee, Ermington (AU)

(73) Assignee: SmithKline Beecham Limited, Brentford, Middlesex (GB)

( * ) Notice: Subject to any disclaimer, the term of this patent is extended or adjusted under 35 U.S.C. 154(b) by 384 days.

(21) Appl. No.: 10/257,077

(22) PCT Filed: Apr. 12, 2001

(86) PCT No.: PCT/EP01/04302
§ 371 (c)(1),
(2), (4) Date: Jun. 6, 2003

(87) PCT Pub. No.: WO01/80834
PCT Pub. Date: Nov. 1, 2001

(65) Prior Publication Data
US 2004/0202716 A1  Oct. 14, 2004

(30) Foreign Application Priority Data

Apr. 19, 2000 (GB) .................................. 0009522.4

(51) Int. Cl.
*A61K 9/20* (2006.01)
(52) U.S. Cl. ........ 424/464; 424/472; 424/484; 424/488; 424/465; 424/468
(58) Field of Classification Search .................... 514/474
See application file for complete search history.

(56) References Cited

U.S. PATENT DOCUMENTS

| | | | |
|---|---|---|---|
| 4,292,298 A * | 9/1981 | Davis | 514/474 |
| 4,946,685 A | 8/1990 | Edgren et al. | |
| 5,009,895 A * | 4/1991 | Lui | 424/465 |
| 5,283,065 A | 2/1994 | Doyon et al. | |
| 5,773,031 A | 6/1998 | Shah et al. | |
| 5,900,425 A | 5/1999 | Kanikanti et al. | |
| 5,945,123 A | 8/1999 | Hermelin | |
| 6,699,502 B1 | 3/2004 | Fanara et al. | |
| 2005/0260267 A1 | 11/2005 | Qasem et al. | |

FOREIGN PATENT DOCUMENTS

| | | | |
|---|---|---|---|
| EP | 0 305 051 | | 3/1989 |
| FR | 2 766 708 | | 2/1999 |
| WO | WO 00/13669 | | 3/2000 |
| WO | WO 00/13670 | | 3/2000 |
| WO | WO 00/13673 | * | 3/2000 |
| WO | WO 00/13678 | | 3/2000 |

OTHER PUBLICATIONS

Siepmann, et al., Pharmaceutical Research, vol. 17(10) pp. 1290-1298 (2000).
Billon, et al., Drug Dev. and Ind. Pharmacy, vol. 25(11) pp. 1149-1156 (1999).
Lee, et al., Int. J. of Pharmaceutics, vol. 188 pp. 71-80 (1999).
Siepmann, et al., Int. J. of Pharmaceutics, vol. 201 pp. 151-164 (2000).
Colombo, Adv. Drug Delivery Reviews, vol. 11 pp. 37-57 (1993).

* cited by examiner

*Primary Examiner* — Robert A Wax
*Assistant Examiner* — Hasan S Ahmed
(74) *Attorney, Agent, or Firm* — Dara L. Dinner; Theodore Furman (57) ABSTRACT

A pharmaceutical composition comprising an immediate release phase and a sustained release phase of paracetamol is described which has a unique in vitro dissolution profile resulting in advantageous pharmacokinetic properties.

27 Claims, 4 Drawing Sheets

SUSTAINED RELEASE PARACETAMOL CONTAINING COMPOSITIONS

The present invention relates to pharmaceutical compositions containing N-acetyl-p-aminophenol, known by the generic names paracetamol, acetaminophen and APAP (hereinafter referred to as paracetamol). In particular, the invention relates to a sustained release paracetamol formulation having an advantageous pharmacokinetic profile.

Paracetamol is an analgesic and antipyretic agent which is widely used in prescription and non-prescription medicines, often in combination with other biologically active compounds.

The elimination half-life of paracetamol is reported to be in the range of 1.9-2.5 hours. Its absorption following oral doses of conventional immediate release tablets is characterised by passive absorption with high bioavailability (80%) and rapidly occurring maximum plasma concentration ($t_{max}$ 30-90 min). These characteristics determine the conventional dosage regimen of 1000 mg every 4 to 6 hours for the drug. Although this regimen is acceptable in the short-term treatment of acute pain, it becomes inconvenient in the context of long-term treatment of sub-chronic or chronic pain. Therefore, extended release paracetamol may improve patient's quality of life by reducing the number of doses to be taken and providing steadier levels of the drug in the blood as determined by plasma or serum drug concentrations.

A paracetamol product designed for tid oral dosing should contain enough paracetamol to give close to the maximum daily dose when two tablets are taken three times daily, ie about 600 mg to 667 mg per tablet.

Such a product is described in EP-A-305051 (McNeil Inc) which discloses a sustained release bilayer tablet containing either 650 or 667 mg of paracetamol. Such prior disclosed tablets contain equal amounts of paracetamol in an immediate release layer and a sustained release layer. The sustained release layer is provided by a matrix comprising a mixture of hydroxyethylcellulose and polyvinyl-pyrrolidone. McNeil Inc markets such a bilayer tablet as Tylenol® Extended Relief in the US.

A sustained release paracetamol oral dosage form designed for tid dosing should also provide all the benefit of immediate release paracetamol plus a sustained action. Therefore an ideal sustained release paracetamol product for oral administration should be suitable for treating both acute pain such as dental pain or headache and chronic pain, such as the pain associated with arthritis.

One potential disadvantage concerning a formulation containing more than the standard dose of paracetamol (500 mg) is accidental or intentional overdose. In such circumstances more paracetamol will be ingested from an extended release formulation compared to a conventional immediate release formulation for any given number of unit doses such as tablets. This could have serious consequences for an overdose patient, especially if a large amount of the dose is absorbed before rescue therapy could be initiated. It would therefore be preferable if the unit dose (such as a tablet) was designed to limit the amount of paracetamol absorbed in the first few hours following dosing. An advantageous sustained release formulation should therefore demonstrate a lower mean. $C_{max}$ (preferably at least 20% lower) than a conventional immediate release formulation which would be indicative of a lower initial exposure.

One possible consequence of formulating an orally administered paracetamol product designed to have a lower $C_{max}$ and slower rate of absorption, is that the extent of absorption may also be decreased, this could then lead to sub-therapeutic systemic levels of drug 6-8 hours following dosing thus leading to premature onset of pain before administration of a further dose.

One further advantage for a product designed to have a lower $C_{max}$ and slower rate of absorption where the extent of absorption is essentially complete (as demonstrable by an equivalent dose corrected AUC compared to immediate release tablets) is that it should have the advantage of maintaining therapeutic levels of paracetamol in plasma for extended periods following dosing and hence provide analgesia for longer than a conventional immediate release tablet or capsule. Furthermore as a result of a reduced $C_{max}$, systemic levels of paracetamol are likely to remain at more constant levels, thus benefiting the patient.

Whilst such a formulation should have a lower $C_{max}$ compared to a conventional immediate formulation, it is still desirable to have a fast onset of action, therefore initial levels of drug in plasma should be rapidly attained (preferably within 30 minutes) and maintained at therapeutic levels of >3 mcg/ml for at least 1.3 hours and preferably 1.5 hours longer than a standard immediate release tablet or capsule. In addition the extent of absorption should be equivalent to a conventional immediate release formulation.

Furthermore, upon multiple dosing of a sustained release formulation the steady state plasma levels of paracetamol should be more constant than those achieved following multiple dosing of a conventional immediate release formulation. A convenient measure of the fluctuation in plasma concentrations is the fluctuation index (FI) which is defined as $(C_{max}-C_{min})/C_{average}$. A low FI number (ie <1) is considered to be advantageous as it suggests a reduction in the variability of plasma concentrations indicative of a safer product.

In summary, an advantageous sustained release paracetamol product for oral administration should possess the following pharmacokinetic attributes:

(1) therapeutically active drug plasma concentrations should be attained rapidly.
(2) the mean maximum plasma concentration ($C_{max}$) should be at least 20% lower compared to standard immediate release formulation;
(3) a mean plasma concentration of at least 3 mcg/ml should be maintained for at least 1.3 hours longer (preferably 1.5 hours longer) than a standard immediate release formulation;
(4) the extent of absorption should be equivalent to a conventional immediate release paracetamol;
(5) plasma levels of paracetamol following multiple dosing should be more constant compared to multiple dosing of an immediate release formulation as measured by a reduction in the fluctuation index.

Surprisingly it has now been discovered that such an advantageous pharmacokinetic profile can be provided by a two phase (immediate release and sustained release) formulation of paracetamol which satisfies a unique in vitro dissolution profile.

Accordingly, in a first aspect the present invention provides a pharmaceutical composition, having an immediate release phase and a sustained release phase of paracetamol, said composition comprising from 600 to 700 mg of paracetamol per unit dose and a pharmaceutically acceptable carrier, characterised in having an in vitro paracetamol dissolution profile (as determined by the USP type III apparatus, reciprocating basket, with 250 ml of 0.1M HCl at 37 C set at a cycle speed of 15 strokes/min) with the following constraints:

30 to 48% released after 15 minutes
56 to 75% released after 60 minutes
>85% released after 180 minutes.

Preferably the in vitro dissolution profile has the following constraints:

35 to 47% released after 15 minutes
58 to 73% released after 60 minutes
>90% released after 180 minutes.

Most preferably the in vitro dissolution profile has the following constraints:

38 to 44% released after 15 minutes
62 to 70% released after 60 minutes
>95% released after 180 minutes.

Suitably paracetamol is present in an amount of 630 to 680 mg per unit dose, more preferably in an amount of 650 to 667 mg per unit dose and more preferably in an amount of 665 mg per unit dose, so that a tid dosage regimen will deliver a maximum daily dose of about 4 g of paracetamol when two unit doses are taken three times daily.

Preferred unit dose forms include tablets or capsules.

The immediate release phase and the sustained release phase both contain paracetamol and a pharmaceutically acceptable carrier and are suitably combined together into a unit dose form. For example the immediate release phase and the sustained release phase can be separate blends, granules or pellets which can be mixed together before being compressed into a tablet or being filled into a capsule. A preferred unit dose form is a bilayer tablet having an immediate release layer of paracetamol and a sustained release layer of paracetamol.

Suitably the sustained release phase comprises a matrix-forming polymer to provide a sustained release of paracetamol.

Examples of matrix-forming polymers include both water soluble and water insoluble polymers or mixtures thereof, with soluble polymers being preferred. Examples of water soluble polymers include hydroxypropylmethylcellulose, hydroxyethylcellulose, carboxymethylcellulose, sodium carboxymethylcellulose, methacrylate hydrogels, polyethylene glycols and xanthan gum. An example of a water insoluble polymer is ethylcellulose. A preferred matrix-forming polymer is hydroxypropylmethylcellulose.

The amount of matrix-forming polymer in the sustained release phase and the relative amounts of paracetamol in the sustained release and immediate release phases are selected so as to provide the desired in vitro dissolution rate as hereinbefore described.

Thus, the matrix-forming polymer is suitably present in an amount from 0.5 to 10%, preferably from 1 to 6%, and more preferably from 2 to 4% by weight of the sustained release phase.

Suitably the sustained release phase comprises from 55 to 90% by weight of the total paracetamol, and the immediate release phase comprises from 10 to 45% by weight of the total paracetamol. Preferably the sustained release phase comprises from 60 to 80% by weight of the total paracetamol, and the immediate release phase comprises from 20 to 40% by weight of the total paracetamol. More preferably the sustained release phase comprises from 65 to 75% by weight of the total paracetamol, and the immediate release phase comprises from 25 to 35% by weight of the total paracetamol.

Compositions of the present invention will generally contain at least one pharmaceutically acceptable carrier conventionally used in the art of tablet and/or capsule formulation. Suitable carriers which may be incorporated include lubricants, for example magnesium stearate and stearic acid; disintegrants, for example cellulose derivatives and starches; binders, for example modified starches, cellulose derivatives and polyvinylpyrrolidone; glidants, for example colloidol silicas; compression aids, for example cellulose derivatives; as well as preservatives, suspending agents, wetting agents, flavouring agents, bulking agents, adhesives, colouring agents, sweetening agents appropriate to their form.

In addition to paracetamol, compositions of the invention may also contain other pharmaceutically active agents, for example other analgesics, anti-inflammatory analgesic agents, decongestants, antihistamines, antitussive agents, etc.

Compositions may also contain a pharmaceutically acceptable analgesic adjuvant, for example caffeine.

The compositions of the present invention can be formulated by conventional methods of admixture such as granulating, blending, filling and compressing.

For example tablets can be produced by a wet granulation process, where the immediate release phase and sustained release phase are separately prepared. Suitably, for either the immediate release or sustained release phase, the active drug substance and excipients are screened and mixed in a high shear mixer granulator or fluid bed dryer. The blend is granulated by the addition of a granulating solution (typically purified water, disintegration agent dissolved/dispersed in purified water, or drug dissolved/dispersed in purified water or a suitable solvent) sprayed into the high shear mixer granulator or fluid bed dryer. If desired wetting agents e.g. surfactants can be added. The resulting granules (optionally pelletised) are dried usually with residual moisture of 1-5% by tray, fluid bed or microwave drying techniques. The dried granules are milled to produce a uniform particle size, the granules are blended with extragranular excipients as necessary, typically a lubricant and glidant (e.g. magnesium stearate, silicon dioxide). The separately prepared immediate release and sustained release granules can then be compressed together using a rotary tablet press (such as a bilayer tablet press) typically in the range of 600 to 750 mg. The resulting tablets can be coated in a pan coater typically with a 1-5% aqueous film coat, followed by a wax polishing.

Alternatively tablets can be produced by a direct compression process. Suitably the active drug substance and excipients for the immediate release and sustained release phases are separately screened and mixed in a suitable blender e.g. a cone, cube or V-blender. Other excipients are added as necessary, and further blended. The separately prepared immediate release and sustained release phases can be combined and compressed together using a rotary tablet press as hereinbefore described. The resulting tablets can be coated in a pan coater.

Tablets can also be prepared by using both methods of wet granulation and direct compression. For example the sustained release phase can be prepared by wet granulation as hereinbefore described, whilst the immediate release phase can be prepared by blending the excipients for direct compression. Furthermore commercially available blends of immediate release paracetamol are also available for direct compression such as DC90 paracetamol supplied by Rhone Poulenc. The two phases can then be combined and compressed together as hereinbefore described.

Suitably capsules can be produced by separately preparing the immediate release and sustained release phases by screening and mixing the active drug substance and excipients in a suitable blender e.g. a cone, cube or V-blender. Other excipients are added as necessary, typically a lubricant and glidant, and the mixture blended. The separately prepared immediate release and sustained release phased can then be blended and filled into capsules with a fill weight typically ranging from 600 to 750 mg using a standard capsule filling machine.

The following Examples illustrate the advantageous properties of the compositions of the present invention.

EXAMPLE 1

This Example compares the properties of a commercially available immediate release 500 mg paracetamol tablet with two prototype sustained release bilayer tablets (Formulations A and B) which both have an in vitro dissolution profile outside the scope of the present invention.

These prototype tablets containing a total of about 650 mg of paracetamol were prepared from the following ingredients:

| Ingredient | Tablet Formulation A | | Tablet Formulation B | |
|---|---|---|---|---|
| | mg/tablet | % w/w | mg/tablet | % w/w |
| Sustained Release Layer | | | | |
| Paracetamol | 264.08 | 34.75 | 403.39 | 52.10 |
| High viscosity HPMC | 18.96 | 2.49 | 28.96 | 3.74 |
| Pregelatinised Starch | 21.05 | 2.77 | 32.15 | 4.15 |
| Polyvinylpyrrolidone | 5.88 | 0.77 | 8.98 | 1.16 |
| Low viscosity HPMC | 5.09 | 0.67 | 7.77 | 1.00 |
| Magnesium Stearate | 0.95 | 0.12 | 1.45 | 0.19 |
| Immediate Release Layer | | | | |
| Directly compressible paracetamol granulation DC90# | 436.00 | 57.36 | 283.5 | 36.62 |
| (Paracetamol content in DC90) | (389.80) | (51.28) | (260.00) | (33.58) |
| Film and Wax Coating | 8.05 | 1.06 | 8.05 | 1.04 |
| Total | 760.05 | 100.000 | 774.25 | 100.00 |
| % w/w SR:IR APAP | 41.1:59.9 | | 60.5:39.5 | |

DC90 is a commercially available directly compressible paracetamol granulation containing about 90% by weight of paracetamol together with pregelatinised starch, croscarmellose sodium, polyvinylpyrrolidone and stearic acid.

The release profiles of test formulations A and B were characterised using the USP type III apparatus (reciprocating basket) with 250 ml 0.1M HCl at 37 C set at a cycle speed of 15 strokes/min. Both formulations comprised an immediate release component which released within the first fifteen minutes and a sustained release component that released slowly after 15 minutes as detailed in table 1.

TABLE 1

Dissolution profiles for tablets A and B

| | % paracetamol released | |
|---|---|---|
| Time in minutes | Prototype A Paracetamol 650 mg Sustained Release | Prototype B Paracetamol 650 mg Sustained Release |
| 15 minutes | 51.3 | 39.1 |
| 60 minutes | 71.2 | 54.7 |
| 120 minutes | 87.0 | 68.7 |
| 180 minutes | 99.3 | 79.4 |
| 240 minutes | 103.7 | 89.4 |
| 300 minutes | | 96.0 |
| 360 minutes | | 97.3 |

Figure 1:
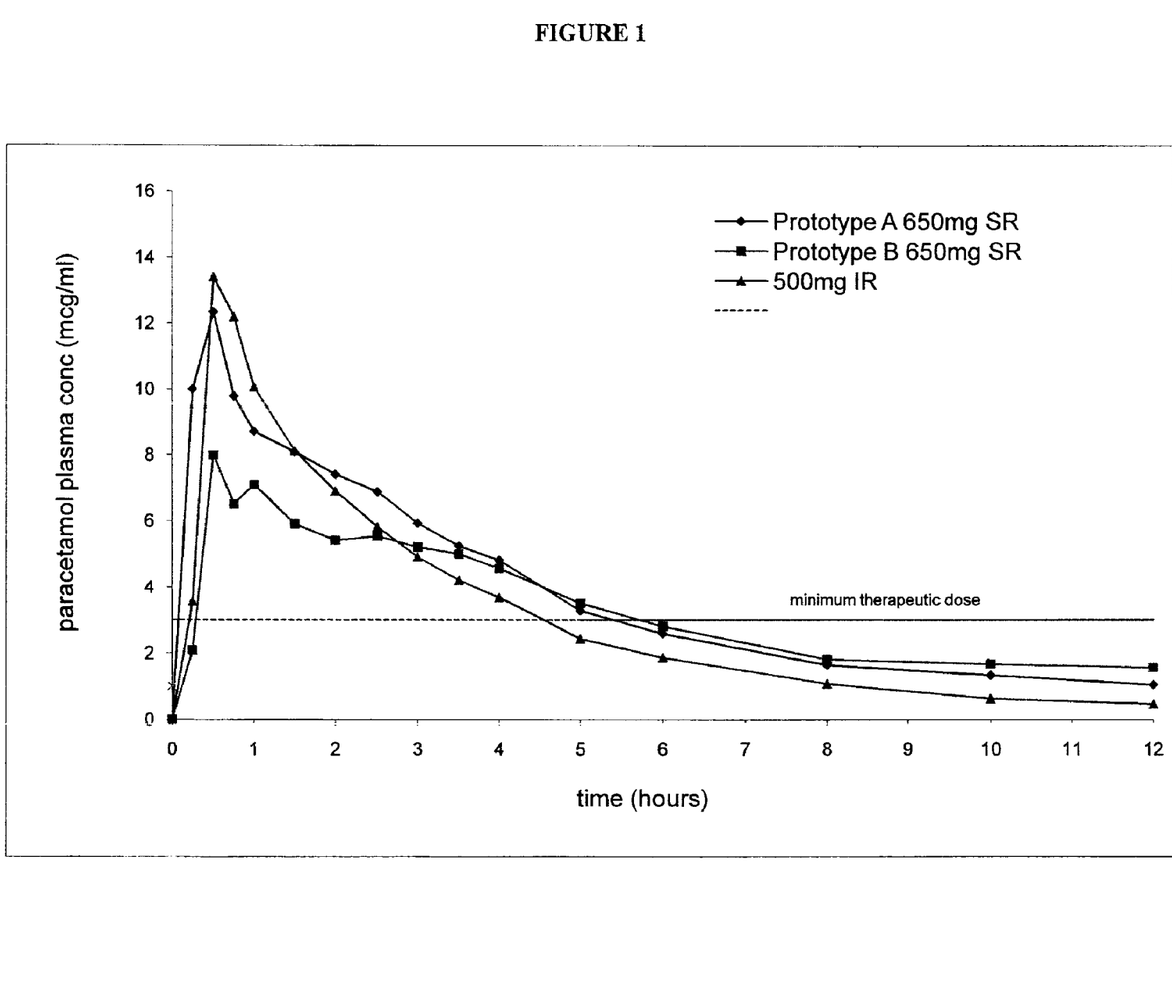
FIG. 1 shows the mean pharmacokinetic profiles of Tablet A, Tablet B and a 500 mg immediate release paracetamol tablet.

The two prototype formulae were assessed in a pharmacokinetic study in healthy fasted volunteers. The study design was three-way crossover involving six volunteers, using paracetamol 500 mg immediate release tablets as a control. The mean pharmacokinetic profiles are shown in FIG. 1.

The results from the biostudy demonstrated that neither formulation A or B met the criteria of achieving a mean paracetamol plasma concentration of 3 mcg/ml for at least 1.5 hours longer than the immediate release tablet, with levels of >3 mcg/ml only being maintained for approximately 5.4 hours for formulation A and 5.8 hours for formulation B, compared to 4.6 hours for the reference formula (500 mg immediate release paracetamol tablets).

The mean $C_{max}$ values for Formulation A and formulation B were 15.0 and 9.6 mcg/ml respectively compared to 17.3 mcg/ml for the 500 mg immediate release tablet and the mean dose corrected AUC values were 45.9 mcg hr/ml for formulation A, 40.1 mcg hr/ml for formulation B and 49.3 mcg hr/ml for the 500 mg immediate release tablet. The lower AUC value observed for Formulation B was indicative of a reduced extent of absorption.

EXAMPLE 2

This Example compares the properties of a commercially available immediate release 500 mg paracetamol tablet with a sustained release bilayer tablet (Formulation C) having an in vitro dissolution profile falling within the scope of the present invention.

This advantageous bilayer tablet containing a total of 666.6 mg of paracetamol was prepared from the following ingredients:

| Ingredient | Tablet Formulation C | |
|---|---|---|
| | mg/tablet | % w/w |
| Sustained Release Layer | | |
| Paracetamol | 473.57 | 64.39 |
| High viscosity HPMC | 15.43 | 2.10 |
| Pregelatinised Starch | 5.14 | 0.70 |
| Polyvinylpyrrolidone | 10.28 | 1.40 |
| Low viscosity HPMC | 8.23 | 1.12 |
| Magnesium Stearate | 1.54 | 0.21 |
| Immediate Release Layer | | |
| Directly compressible paracetamol granulation DC90 | 214.92 | 29.22 |
| (Paracetamol content in DC90) | (193.43) | (26.30) |
| Film and Wax Coating | 6.305 | 0.86 |
| Total | 735.42 | 100.00 |
| % w/w SR:IR APAP | 71:29 | |

The release profile of test formulation C was characterised using the USP type m apparatus (reciprocating basket) as hereinbefore described and was found to have the following dissolution rate as detailed in table 2.

TABLE 2

Dissolution Profile for Formulation C

| Time (minutes) | In-vitro release Results (% paracetamol released) |
| --- | --- |
| 15 | 39.4% |
| 60 | 64.4% |
| 120 | 89.0% |
| 180 | 101.8% |

Figure 2:
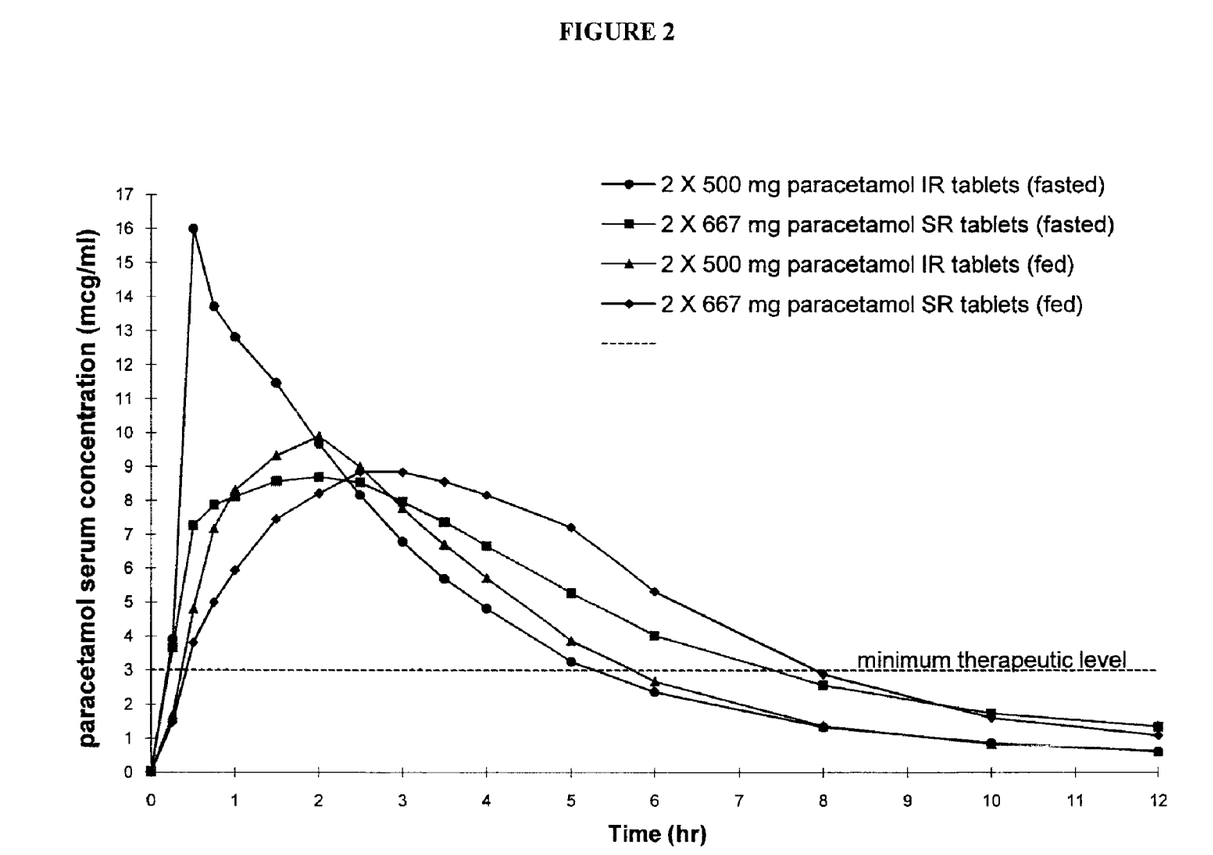
FIG. 2 shows mean pharmacokinetic profiles as described therein.

Formulation C was assessed in a pharmacokinetic study. The study design was a four-way crossover, using a panel of 26 healthy volunteers which compared the pharmacokinetics of paracetamol in serum in both fed and fasted states following a two tablet dose of the formula C and a two tablet dose of a currently marketed standard immediate release paracetamol 500 mg tablet. The mean pharmacokinetic profiles are shown in FIG. 2.

Formulation C met all of the pharmacokinetic criteria outlined above for an ideal sustained release paracetamol tablet. The pharmacokinetic analysis demonstrated that the $C_{max}$ was significantly lower for formulation C (mean value 10.1 mcg/ml) to the reference immediate release product (mean value 18.7 mcg/ml) (in the fasted state). In addition therapeutic serum concentrations were rapidly attained and mean serum levels of 3 mcg were maintained until 7.4 hours post dose compared to only 5.3 hours post dose for the 500 mg immediate release tablet. The two formulae were bioequivalent with respect to AUC indicating that the extent of absorption was the same for formulation C as for conventional immediate release paracetamol.

These advantageous properties of formulation C are particularly surprising when compared with the plasma concentrations described in Example 1 of EP-A-305051 which suggests that the $C_{max}$ of the prior disclosed sustained release paracetamol formulation is as high as that observed for an immediate release formulation

EXAMPLE 3

This Example compares the properties of a commercially available immediate release 500 mg paracetamol tablet with another sustained release bilayer tablet (Formulation D) having an in vitro dissolution profile falling within the scope of the present invention.

The bilayer tablet of Formulation D was essentially similar to Formulation C but contained a total of 665 mg of paracetamol and had a slightly different ratio of sustained release to immediate release paracetamol (% w/w SR:IR APAP was 69:31).

The release profile of test formulation D was characterised using the USP type III apparatus (reciprocating basket) as hereinbefore described and was found to have the following dissolution rate as detailed in table 3.

TABLE 3

Dissolution Profile for Formulation D

| Time (minutes) | In-vitro release Results (% paracetamol released) |
| --- | --- |
| 15 | 40.8% |
| 60 | 65.0% |

TABLE 3-continued

Dissolution Profile for Formulation D

| Time (minutes) | In-vitro release Results (% paracetamol released) |
| --- | --- |
| 120 | 90.2% |
| 180 | 101.8% |

Formulation D was assessed in a further biostudy which involved 27 subjects. The study was an open multiple dose crossover in healthy subjects. There were two study sessions each consisting of two days of dosing with a 24 hour blood sampling on the second day. The study sessions were separated by 48 hours.

The two study treatments were as follows:
  2 bilayer sustained release (SR) tablets of formulation D each containing 665 mg given three times per day (every 8 hours).
  2 immediate release (IR) paracetamol 500 mg tablets given four times per day (every 6 hours).

Figure 3:
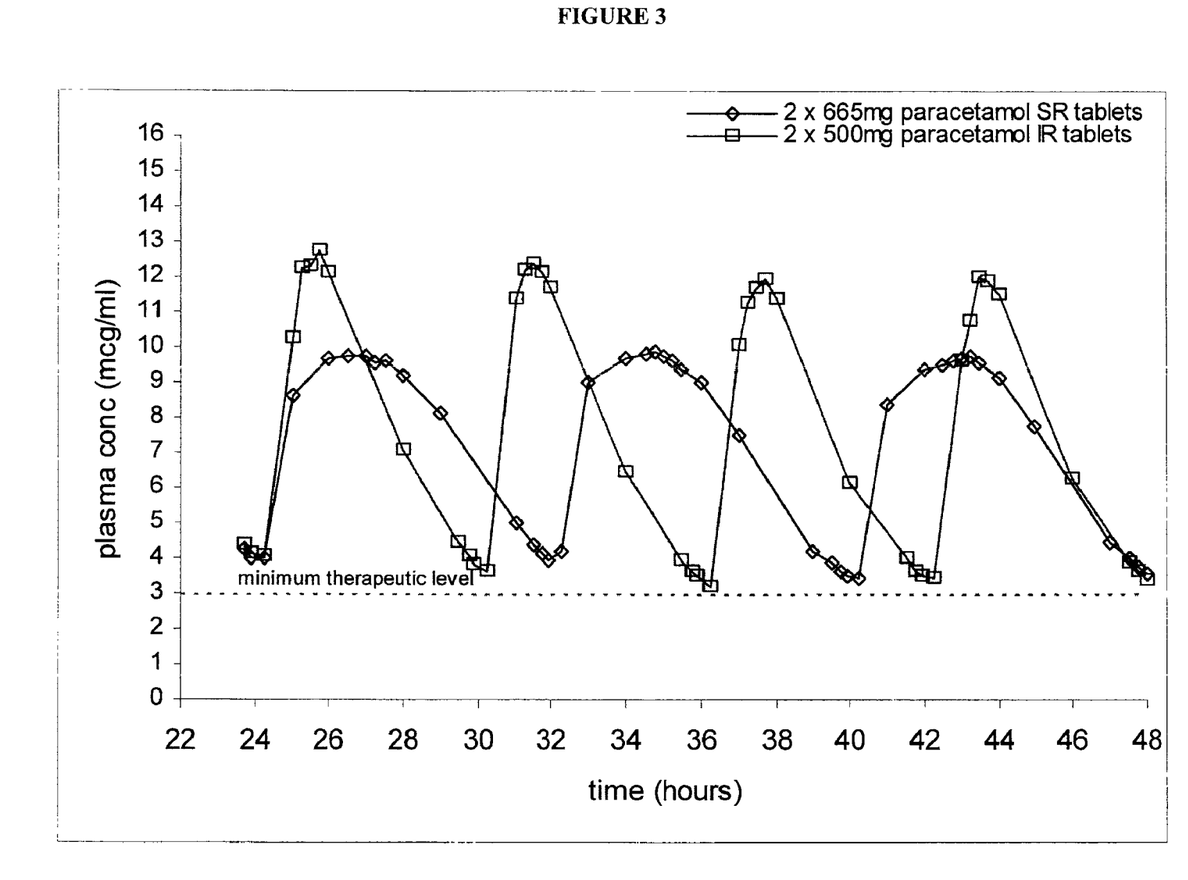
FIG. 3 shows mean plasma paracetamol concentrations versus time as described therein.

Pharmacokinetic analysis was conducted for the period of 24 hours-48 hours following commencement of the dosing schedule. The results showed that the two treatments were bioequivalent with respect to $AUC_{24-48}$ and the SR formulation provided a lower $C_{max}$ a higher $C_{min}$ and a substantially lower fluctuation index (FI) compared to the immediate release formulation. The values for FI were 0.957 for the SR tablet and 1.388 for the immediate release paracetamol tablet. The difference was highly significant (P<0.001). Mean plasma paracetamol concentrations versus time are shown in FIG. 3.

Figure 4:
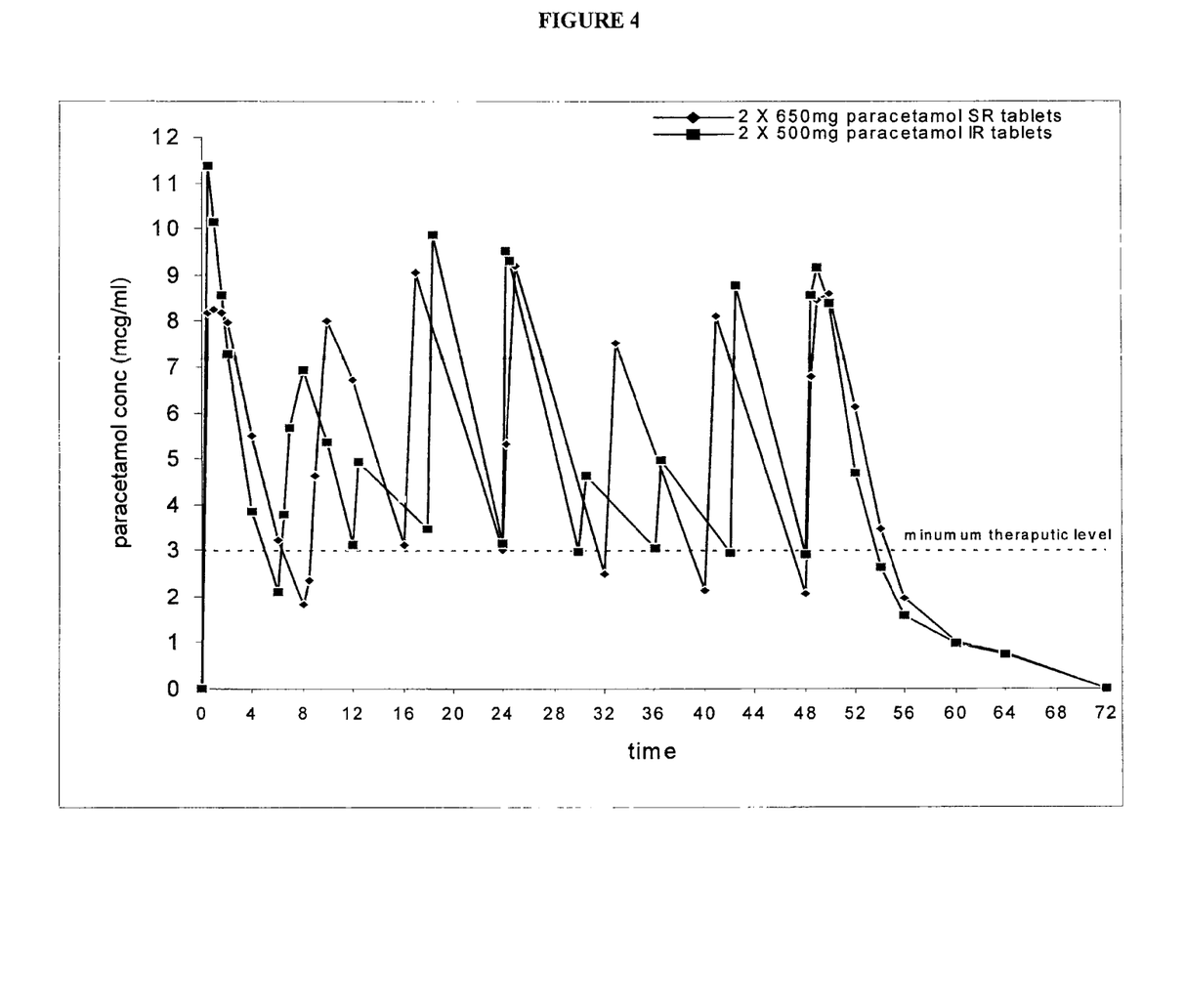
FIG. 4 shows the fluctuation index for an SR and an IR product as described therein.

The substantially lower FI for the SR product is surprising considering previous reports for a steady state biostudy conducted with a 650 mg bilayer tablet (Tylenol Extended Relief) which showed that the SR product had a numerically higher FI (of 1.49) compared to a reference 500 mg IR tablet (of 1.44) as illustrated in FIG. 4. Furthermore, Paracetamol plasma levels were maintained substantially above 3 mcg/ml for the entire study period, which is in contrast to the steady state study reported for Tylenol® Extended relief.

The low FI number of <1 found for formulation D, is particularly advantageous for a sustained release formulation as it indicates a reduction in the variability of plasma concentration suggesting a much safer and more reliable product.

EXAMPLE 4

The example compares the clinical properties of a commercially available paracetamol 500 mg immediate release (IR) tablet with a sustained release (SR) bilayer tablet of Formulation D.

The study was a multicentre, single dose, double-blind, double dummy, two armed parallel group efficacy study involving 510 patients with post-surgical dental pain following third molar extraction under general anesthesia to compare the efficacy of a 2 tablet dose of either a sustained release tablet containing 665 mg paracetamol per tablet (252 patients) or a 2 tablet dose of a commercially available tablet containing 500 mg of immediate release paracetamol per tablet (258 patients).

Patients were randomised to receive one of the two treatments following surgery, when post-surgical dental pain had reached moderate/severe intensity, defined by a recording of 30 mm on a visual analogue scale. Patients remained in the clinic for 4 hours after receiving study medication and completed pain assessments at intervals up to and including 4 hours when a global assessment of pain relief was made. Patients were discharged from the clinic and continued to complete pain assessments at home for 4 hours. If additional analgesia was taken during the 8 hour evaluation period (re-medication), the patient was considered to have completed the study.

Parameters measured during the study were as follows:
Primary Parameter

Overall pain relief: measured on a 5-point verbal scale (poor, fair, good, very good and excellent) 4 hours following treatment.
Secondary Parameters Other pain assessments were made 0, 0.5, 1, 1.5, 2, 3, 4, 5, 6, 7, and 8 hours after treatment (see below). The results provided information on pain relief and pain intensity over time. In addition, time to re-mediation was measured.

Pain relief: based on a 5-point visual rating scale [no relief (0), a little relief (1), some relief (3), a lot of relief (4), complete relief (5)]. The following calculations were made: peak pain relief, time to peak pain relief and total pain relief (at 1, 4, 6 and 8 hours).

Pain intensity difference: based on a 4-point visual rating scale [none (0), mild (1), moderate (2) and severe (3)]. Differences from baseline were calculated. The following calculations were made: peak pain intensity difference, time to peak pain intensity difference and summed pain intensity differences (at 4, 6 and 8 hours).

Pain analogue intensity difference: based on a visual analogue scale from 0 (no pain) to 100 (unbearable pain). Summed pain analogue intensity differences (from baseline) were calculated at 4,6 and 8 hours.
Results Based on the patient global assessment at 4 hours, the extended release product was shown to be equivalent or better than the immediate release product. A successful response was defined as a 'very good' or 'excellent' rating: 88 of 252 (35.1%) patients treated with the SR paracetamol formulation gave a successful response compared with 71 of 258 (27.7%) patients treated with standard IR paracetamol. Equivalence was concluded from the 90% confidence interval of the treatment difference (7.3% in favour of SR paracetamol) between the two formulations.

There was no significant difference between SR paracetamol and standard IR paracetamol in either development of analgesia (time to peak pain relief, time to peak pain intensity difference, total pain relief 1 hour after treatment) or peak analgesic effect (peak pain relief, peak pain intensity difference), However, the SR tablet was significantly more effective than standard IR paracetamol for the summed pain analogue intensity difference at 6 hours ($p=0.0344$) and 8 hours ($p=0.0500$). Furthermore, the median time to re-medication was longer for SR paracetamol (245 mins) compared with standard IR paracetamol (190 mins). Although this was not statistically significant, it was clear from the separation of the two curves on the Kaplan-Meier plot that a smaller proportion of patients treated with SR paracetamol re-medicated between approximately 3 and 6 hours compared with standard IR paracetamol.

These results indicated that the SR tablet gave rapid analgesia which was maintained for up to eight hours following dosing and the SR tablet had a longer duration of action than IR paracetamol.

The invention claimed is:

1. A pharmaceutical composition comprising a bilayer tablet having an immediate release phase of paracetamol and a sustained release phase of paracetamol,
   the immediate release phase being in one layer and comprising from about 25 to 35% by weight of the total paracetamol; and
   the sustained release phase being in the other layer, and the sustained release layer comprising paracetamol comprising from about 65 to 75% by weight of the total paracetamol in admixture with a matrix forming water soluble polymer which is selected from two different viscosities of hydroxypropylmethylcellulose present in an amount from 0.5 to 10% by weight of the sustained release phase and wherein the hydroxypropylmethylcellulose is present as a low viscosity hydroxypropylmethylcellulose and a high viscosity hydroxypropylmethylcellulose in a ratio of about 1:2; said composition comprising from 600 to 700 mg of paracetamol per unit dose and
   a pharmaceutically acceptable carrier, characterised in having an in vitro paracetamol dissolution profile (as determined by the USP type III apparatus, reciprocating basket, with 250 ml of 0.1M HCl at 37° C. set at a cycle speed of 15 strokes/min) with the following constraints:
   30 to 48% released after 15 minutes
   56 to 75% released after 60 minutes
   >85% released after 180 minutes.

2. A composition according to claim 1 in which the in vitro dissolution profile
   has the following constraints:
   35 to 47% released after 15 minutes
   58 to 73% released after 60 minutes
   >90% released after 180 minutes.

3. A composition according to claim 1 in which the in vitro dissolution profile has the following constraints:
   38 to 44% released after 15 minutes
   62 to 70% released after 60 minutes
   >95% released after 180 minutes.

4. A composition according to claim 1 in which the paracetamol is
   present in an amount of 630 to 680 mg per unit dose.

5. A composition according to claim 4 in which the paracetamol is present in an amount of 650 to 667 mg per unit dose.

6. A composition according to claim 1 in which the matrix forming water soluble polymer is present in an amount from 1 to 6% by weight of the sustained release phase.

7. A composition according to claim 6 in which the matrix forming water soluble polymer is present in an amount from 2 to 4% by weight of the sustained release phase.

8. A composition according to claim 1 in which the sustained release phase comprises from 64% by weight of the total paracetamol.

9. A composition according to claim 8 in which the immediate release component comprises about 29% by weight of the total paracetamol.

10. A pharmaceutical composition comprising a bilayer tablet having an immediate release phase and a sustained release phase of paracetamol, the immediate release phase being in one layer and the sustained release phase being in the other layer, said composition comprising from 600 to 700 mg of paracetamol per unit dose, and wherein the sustained release layer comprises a mixture of at least two hydroxypropylmethylcellulose polymers each having a different the first polymer having a low viscosity and the second polymer having a high viscosity and present in a ratio of about 1:2, characterized in having an in vitro paracetamol dissolution profile (as determined by the USP type III apparatus, reciprocating basket, with 250 ml of 0.1M HCl at 37° C. set at a cycle speed of 15 strokes/min) with the following constraints:
30 to 48% released after 15 minutes
56 to 75% released after 60 minutes
>85% released after 180 minutes; and
said composition providing a mean plasma concentration of at least 3 mcg/ml for at least 1.3 hours longer than a 500 mg paracetamol containing immediate release formulation.

11. A composition according to claim 10 in which the in vitro dissolution profile has the following constraints:
35 to 47% released after 15 minutes
58 to 73% released after 60 minutes
>90% released after 180 minutes.

12. A composition according to claim 10 in which the in vitro dissolution profile has the following constraints:
38 to 44% released after 15 minutes
62 to 70% released after 60 minutes
>95% released after 180 minutes.

13. A composition according to claim 10 in which the paracetamol is present in an amount of 630 to 680 mg per unit dose.

14. A composition according to claim 13 in which the paracetamol is present in an amount of 650 to 667 mg per unit dose.

15. A composition according to claim 10 in which the hydroxypropylmethylcellulose polymers are present in an amount from 0.5 to 10% by weight of the sustained release phase.

16. A composition according to claim 15 in which the hydroxypropylmethylcellulose polymers are in an amount from 1 to 6% by weight of the sustained release phase.

17. A composition according to claim 16 in which the hydroxypropylmethylcellulose polymers are in an amount from 2 to 4% by weight of the sustained release phase.

18. A composition according to claim 16 in which the sustained release phase comprises from 55 to 90% by weight of the total paracetamol, and the immediate release phase comprises from 10 to 45% by weight of the total paracetamol.

19. A composition according to claim 18 in which the sustained release phase comprises from 60 to 80% by weight of the total paracetamol, and the immediate release phase comprises from 20 to 40% by weight of the total paracetamol.

20. A composition according to claim 19 in which the sustained release component comprises from 65 to 75% by weight of the total paracetamol, and the immediate release component comprises from 25 to 35% by weight of the total paracetamol.

21. A pharmaceutical composition, in the form of a bilayer tablet, having an immediate release phase and a sustained release phase of paracetamol,
the immediate release phase being in one layer and the sustained release phase being in the other layer, said composition comprising from 600 to 700 mg of paracetamol per unit dose, and
wherein the sustained release layer comprises a mixture of at least two hydroxypropylmethylcellulose polymers each having a different the first polymer having a low viscosity and the second polymer having a high viscosity and present in a ratio of about 1:2, characterized in having an in vitro paracetamol dissolution profile (as determined by the USP type III apparatus, reciprocating basket, with 250 ml of 0.1M HCl at 37° C. set at a cycle speed of 15 strokes/min) with the following constraints:
30 to 48% released after 15 minutes
56 to 75% released after 60 minutes
>85% released after 180 minutes; and
said composition providing a Cmax which is lower than, and a high Cmin as compared to a 500 mg paracetamol immediate release formulation.

22. A composition according to claim 21 in which the hydroxypropylmethylcellulose polymers are hydroxypropylcellulose is present in an amount from 0.5 to 10% by weight of the sustained release phase.

23. A composition according to claim 22 in which the hydroxypropylmethylcellulose polymers are hydroxypropylcellulose is present in an amount from 1 to 6% by weight of the sustained release phase.

24. A composition according to claim 23 in which the hydroxypropylmethylcellulose polymers are hydroxypropylcellulose is present in an amount from 2 to 4% by weight of the sustained release phase.

25. A composition according to claim 10 in which the sustained release phase comprises from about 65 to 75% by weight of the total paracetamol.

26. A composition according to claim 1 wherein the sustained release phase comprises paracetamol present in an amount of about 64% w/w, high viscosity hydroxypropylmethylcellulose present in an amount of about 2 w/w and low viscosity hydroxypropylmethylcellulose present in an amount of about 1 w/w.

27. A composition according to claim 26 wherein the immediate release phase comprises paracetamol present in an amount of about 29% w/w.

\* \* \* \* \*